United States Patent [19]
Bergquist et al.

[11] Patent Number: 5,922,934
[45] Date of Patent: Jul. 13, 1999

[54] POLLINATORS FOR TOPCROSS® GRAIN PRODUCTION

[75] Inventors: Richard Robert Bergquist, El Paso, Ill.; Stuart Leonard Kaplan, Clive, Iowa; Douglas Stuart Nubel, Bloomington, Ill.; Terry J. Foley, Willimsburg, Iowa

[73] Assignee: Optimum Quality Grains, L.L.C., West Des Moines, Iowa

[21] Appl. No.: 08/829,066

[22] Filed: Mar. 31, 1997

[51] Int. Cl.$^6$ .............................. A01H 5/00; A01H 4/00; C12N 5/04

[52] U.S. Cl. .................... 800/320.1; 800/298; 800/275; 800/271; 800/264

[58] Field of Search .................................. 800/275, 264, 800/320.1; 435/412, 424, 430, 430.1

[56] References Cited

U.S. PATENT DOCUMENTS 4,798,735   1/1989   Friedman et al. .

OTHER PUBLICATIONS

Poehlman, J. M. *Breeding Field Crops*, 3rd Edition; Avi Publishing Company: Westport, CT, 1987.

Glover, D. V. and Mertz, E. T. In *Nutritional Quality of Cereal Grains: Genetic and Agronomic Improvement*; Olson, R. A. and Frey, K. J., Eds.; American Society of Agronomy: Madison, 1987; pp. 183–336.

Rooney, L. W. and Serna–Saldivar, S. O. In *Corn: Chemistry and Technolgy*; Watson, S. A. and Ramstead, P. E., Eds; American Association of Cereal Chemists, Inc.: St. Paul, 1987; pp. 399–429.

Plant Biotechnology, Feb. 1991, Office of Biotechnology, Iowa State University, Ames, Iowa.

Han, Y., et al. (1987) *Poultry Science* 66:103–111.

Creech, R. and Alexander, D. E. In *Maize Breeding and Genetics*; D. B. Walden, Ed.; John Wiley and Sons: New York, 1978; pp. 249–264.

Iowa Corn Growers Association, 1989, Higher Processing Value in 1989 State Fair Open Class Corn and Soybeans. Bulletin, Aug. 27, 1989.

Alexander, D. E. In *Proceedings of the 43rd Annual Corn and Sorghum Industrial Research Conference*, 1988; pp. 97–105.

Dudley, J. W. et al. In *Seventy Generations of Selection for Oil and Protein in Maize*, Dudley, J. W., Ed. Crop Science Society of America: Madison, 1974; pp. 181–212.

Silvela, L. et al. (1989) *Theoretical and Applied Genetics* 78:298–304.

*Primary Examiner*—Gary Benzion
*Attorney, Agent, or Firm*—Bullwinkel Partners, Ltd.

[57] ABSTRACT

A class of corn plants has been developed that are superior as pollinators in the TopCross® Grain Production System. The plants of this class are larger and more vigorous than many of the current TC Blend® pollinators. The seed that produces this new class of TC Blend® pollinators is produced at greater yields and is of greater vigor and quality than that of many current TC Blend® pollinators. Additionally, the means whereby the seed of this class of plants is produced enables the rapid generation of a wide range of maturities of TC Blend® pollinators. This greatly expands both the geographic range and the genetic breadth of the TopCross® grain production system.

4 Claims, No Drawings

POLLINATORS FOR TOPCROSS® GRAIN PRODUCTION

FIELD OF THE INVENTION

This invention relates to novel corn varieties referred to as "3:1 grain production high oil pollinators". More specifically, this invention concerns the development and utilization of novel 3:1 grain production high oil corn plants as pollinators in the TopCross® grain production system.

BACKGROUND OF THE INVENTION

Corn is a major crop used as a human food source, an animal feed and as a source of carbohydrate, oil, protein and fiber. It is principally used as an energy source in animal feeds or as a raw material for the recovery of starch, protein feed fractions, fiber, flaking grits, flour and oil. The number of products produced from corn or components extracted from corn are numerous and include, among others, (i) paper sizings, high fructose corn syrup, adhesives, food thickeners, industrial and medical absorbents and ethanol (from starch); (ii) animal feed and feed components (from whole grain, corn silage, corn gluten feed and meal); and (iii) corn oil (from germ).

Virtually all corn produced in the United States, Canada and Europe and much of the corn produced in South America is produced from hybrid seed. The production of corn hybrids requires the development of corn inbred lines that demonstrate good general and specific combining ability to produce agronomically superior hybrids. Among the traits that plant breeders select for in producing hybrids are high yield potential, good stalk strength, resistance to specific diseases, drought tolerance, rapid dry down and grain quality sufficient to allow storage and shipment to market with minimum loss. The development of these inbreds is both labor and capital intensive, requiring many years for development, followed by evaluation in many different environments. The incorporation of additional traits that further enhance grain quality places additional constraints on the plant breeder, dramatically increasing the time for development of quality corn inbreds.

Once inbreds have been developed, they may be used in several ways to produce F1 hybrid seed. The majority of F1 hybrid seed produced in the United States is of the single cross type. Two inbred lines are intermated to give rise to what is termed an F1 single cross hybrid (A×B). In some instances, the female parent in the cross is itself an F1 hybrid, so that a three-way cross hybrid is produced with the genotype of (A×B)×C. More rarely, a four-way cross hybrid is produced, with both male and female parents as F1 hybrids, resulting in a genotype of (A×B)×(C×D). In all cases, the resulting kernels from this intermating are sold as seed to growers who ultimately harvest F2 grain from the crop for on farm use or sale. A general review of these systems is available in several texts (e.g., Poehlman, J. M. Breeding Field Crops, 3rd Edition; Avi Publishing Company: Westport, Conn., 1987).

In addition to possessing the proper combination of genetic traits to produce hybrids, the inbreds themselves must be reasonably vigorous to support the demands of modern seed production. This can be illustrated by a description of how single cross hybrids are produced. To control the direction of pollination and assure the harvest of hybrid F1 seed, seed production fields are typically designed so that four rows of inbred corn plants serving as females alternate with one row of inbred corn plants serving as males or pollinators, although other planting patterns that permit the harvest of F1 hybrid seed that is not mixed with the pollinator are possible. The female plants are rendered male sterile either by mechanical detasseling or by biological mechanisms such as cytoplasmic male sterility which renders the tassel nonfunctional. Ovules borne on these female plants are then fertilized by pollen produced by the pollinators that were sown in separate rows to permit the harvest of the F1 hybrid seed. The resulting hybrid seed borne on the female plants (i.e., the seed parents or the seed parent lines) is harvested, cleaned, sized and treated prior to sale to growers. To produce hybrid seed, the pollinator plants need to shed sufficient pollen to fertilize the female plants over a variety of climactic conditions. The hybrid seed borne on the female inbred plants need to be of high quality to allow good germination and early plant vigor in the grower's field and the female plants themselves need to stand and retain ears until the time of harvest. These requirements of the inbred lines themselves further increase the time and money required to develop successful hybrids.

Thus, the capital- and time-intensive development and testing of inbreds are paramount to modern corn production. There are three breeding schemes commonly used to produce inbred lines of corn: the pedigree system of breeding, backcross conversion and recurrent selection. In a commonly practiced form of the pedigree method, two inbred lines of corn, often with different sets of desirable characteristics, are intermated and superior plants are selected and selfed in succeeding generations to become increasingly inbred. Part of this selection procedure involves a periodic assessment of the performance of the emerging inbred lines in various hybrid combinations. The process of continued selfing and selection, typically over five to eight generations, results in the production of lines which are, to a significant degree, genetically homogeneous or inbred. Development and production of an inbred by this method typically takes from 5 to 7 years.

A second method of breeding is backcross conversion, wherein a desired characteristic (generally, one which is simply inherited, such as disease resistance) is introduced into a target inbred (the recurrent parent) by intermating the recurrent parent with a source plant expressing a particular trait of interest. This source plant may also be an inbred, but in the broadest sense can be a member of any plant variety or population cross-fertile with the recurrent parent. The progeny of this cross are then backcrossed (and sometimes selfed) to the recurrent parent, desirable progeny identified and the cycle is repeated. After five to eight cycles of backcrossing and selection, these procedures result in the recovery of the desired characteristic in what is substantially the genetic background of the recurrent parent. Oftentimes the "converted" inbred can be recovered and produced quickly (three to five years) but since the end product is essentially an "older" line in many respects, backcross conversion is generally considered to be a conservative method of inbred development.

The third method of inbred development, recurrent selection, generally involves the extraction of a new inbred from a broad, genetically heterogeneous breeding pool, commonly termed a population. Individual plants within the population are selected for traits of interest such as stalk strength or combining ability and intermated to create a new population from which again to select and intermate individuals with these desired characteristics. Because the number of possible genetic combinations within these populations is quite large, substantial opportunity exists for recovering subpopulations and eventually inbreds with novel grain, seed or whole plant characteristics. However, an inevitable consequence of this genetic diversity is that it takes substantially longer to develop inbreds by recurrent selection than by the preceding two methods.

In summary, all three of the currently available strategies are labor and capital intensive. Each requires many years of effort to allow for both recombination of genetic information and selection to produce inbred lines which would combine to yield hybrid seed which would be sown to produce grain. The rapidity with which satisfactory inbred lines can be developed is determined to a large degree by the nature and number of traits that the lines must possess. The addition of novel or unusual traits, especially if they are controlled by several genes, would significantly increase the time and effort required to produce the desired lines.

Most corn grain is sold and distributed as a commodity, since many of the industrial and animal feed requirements for corn can be met by common varieties of field corn which are widely grown and produced in volume. However, there exists at present a growing market for corn with special end-use properties which are not met by corn grain of standard composition. Most commonly, such "specialty" corn is differentiated from "normal" field corn by altered endosperm properties, such as an overall change in the degree of starch branching (waxy corn, amylose extender; Glover, D. V. and Mertz, E. T. In *Nutritional Quality of Cereal Grains. Genetic and Agronomic Improvement*; Olson, R. A. and Frey, K. J., Eds.; American Society of Agronomy: Madison, 1987; pp. 183–336), increased accumulation of sugars or water-soluble polysaccharides (sugary, shrunken, supersweet corn; Glover, D. V. and Mertz, E. T., supra) or alterations in the degree of endosperm hardness (food grade corn, popcorn; Glover, D. V. and Mertz, E. T., supra; Rooney, L. W. and Serna-Saldivar, S. O. In *Corn: Chemistry and Technology*; Watson, S. A. and Ramstead, P. E., Eds.; American Association of Cereal Chemists, Inc.: St. Paul, 1987; pp. 399–429). Specialty corn types are typically grown under contract for production for specific end users who place value on starch quality or other specific kernel quality attributes. An example of this differentiation is the contract production of waxy maize, whereby inclusion of a single homozygous recessive gene (wx) converts normal maize starch (75–80% amylopectin, 20–25% amylose) nearly completely to amylopectin (>99%). In a similar fashion, the recessive gene amylose extender (ae) when homozygous or the dominant gene Ae-5180 when homozygous or heterozygous (Plant Biotechnology, February 1991, Office of Biotechnology, Iowa State University, Ames, Iowa) increases the specific amylose concentration of the corn grain to 50% or greater. Additionally, U.S. Pat. No. 4,798,735 teaches how modified corn starches produced by combinations of simple recessive genes can result in the production of starch with functional properties optimally suited for use in the food industry. Sweet corn is yet another example of a specialty corn product often grown under contract, where the inclusion of the recessive genes sugary, shrunken-2 or sugary enhancer, singly or in combination, confers sweetness through a reduction in the amount of starch and an increase in the amount of glucose, sucrose and/or water soluble polysaccharides normally found in the immature corn kernel (Creech, R. and Alexander, D. E. In *Maize Breeding and Genetics*; D. B. Walden, Ed.; John Wiley and Sons: New York, 1978; pp. 249–264).

More recently, there is a trend to differentiate corn not only on the basis of alterations in carbohydrate quality but also on the basis of its protein, oil and kernel hardness characteristics. Protein and oil concentration are particularly important determinants of the performance of corn as a component of animal feed (Glover, D. V. and Mertz, E. T., supra; Han, Y., et al. (1987) *Poultry Science* 66:103–111). Furthermore, as coproducts of wet and dry milling, corn oil and protein are important sources of revenue to wet and dry millers. Recent Iowa State University corn performance trials provide a means for recognizing the industrial value of these corn constituents by reporting not only the yield of tested hybrids but also their calculated wet milling and feed values (Iowa Corn Growers Association, 1989, Higher Processing Value in 1989 State Fair Open Class Corn and Soybeans. Bulletin, Aug. 27, 1989).

The breeding, development and nutritional attributes of high oil corn are described below as illustrative of the state of development, heritability, breeding difficulty and economic advantage attendant to the development of many if not all enhanced quality grain traits. Perhaps the most thoroughly studied high oil corn populations are the Illinois High Oil (IHO) and Alexander High Oil (Alexho) populations developed at the University of Illinois. IHO was developed by modified mass selection within the open pollinated corn variety, Burr's White, over more than 80 cycles of selection commencing in 1896 (Alexander, D. E. In *Proceedings of the* 43rd *Annual Corn and Sorghum Industrial Research Conference*, 1988; pp. 97–105; Dudley, J. W. et al. In *Seventy Generations of Selection for Oil and Protein in Maize*, Dudley, J. W., Ed. Crop Science Society of America: Madison, 1974; pp. 181–212). The highest average kernel or grain oil concentration achieved in this population is about 22% oil on a dry weight basis. In contrast, Dr. Denton Alexander, employing both mass and single kernel selection within a synthetic population (Alexho), was able to achieve an average oil concentration of approximately 22% following 28 cycles of selection (Alexander, supra). A number of corn inbreds have been released from the IHO (R802A) and Alexho (R805, R806) populations and are available to the public through the Director of Agricultural Experiment Station, University of Illinois, Urbana, Ill. None of the IHO or Alexho high oil corn populations have resulted in commercially competitive hybrid varieties.

Oil concentration in corn is a grain quality attribute that is quantitatively inherited (Silvela, L. et al. (1989) *Theoretical and Applied Genetics* 78:298–304). Several studies indicate that oil concentration of bulked F2 kernels arising from crosses between various Alexho derivatives and inbred lines of normal oil concentration approaches the midparent value of oil concentration of kernels arising from the self-pollination of each parent separately (Alexander, supra; Misevic, D., A. et al. (1989) *Crop Sci.* 29:613–617). Additionally, F2 grain arising from crossing high-oil and low-oil varieties has been observed to segregate for oil concentration on an individual kernel basis (Alexander, supra). Both of these characteristics are consistent with the hypothesis that oil concentration in corn seed or grain is controlled by the action of several genes, each of which makes a partial contribution to the overall oil concentration. The manipulation of these multiple oil genes makes plant breeding of inbreds for the production of high-oil hybrid seed particularly challenging and time consuming.

Because the genetic heterogeneity is kept high during the initial phases of most recurrent selection programs, it takes substantially longer to develop an agronomically useful inbred from a recurrent selection program than from a program based on pedigree breeding. To date, the majority of high oil corn exists as populations exhibiting varying degrees of genetic nonuniformity. Despite efforts over the last thirty years to develop high oil corn varieties by a combination of recurrent selection and pedigree breeding methods, only a small number of successful high oil inbreds have been produced and only a limited number of high oil hybrid varieties have been grown on any scale.

The widespread demand for high oil corn to meet the needs of poultry, swine, dairy and beef producers is increasingly being met by acceptance of the TopCross® grain production system. The TopCross® system is a novel method for the production of corn grain containing enhanced quality grain traits. The method results in the production of grain with enhanced quality traits following the pollination of high yielding plants by plants containing genes for enhanced quality grain traits. High oil corn grain produced by TopCross® now represents the largest acreage of corn currently grown in the United States other than what is commonly referred to as commodity corn grain. In other words, the acreage devoted to the TopCross® system exceeds that of white corn, waxy corn, high amylose corn or sweet corn. The pollinator plants with enhanced quality grain traits need not be genetically homozygous (inbred) or even homogeneous in appearance and need not be selected for combining ability with high yielding female plants. In this way, the breeding timeline for the production of successful enhanced quality grain trait pollinators is significantly and dramatically reduced and the production of grain with enhanced quality traits is greatly accelerated. This method has catalyzed a great expansion in the number of available agronomically useful female plants that are being used for the production of grain incorporating enhanced quality traits, thus increasing both the yield and the production range of corn varieties expressing enhanced quality grain traits.

The current TC Blend® pollinators used in the TopCross® system may be described as either synthetics or F1 hybrids of synthetics (i.e., synthetic hybrids). They contribute high-oil genes to the developing kernel of the TC Blend® grain parent plant, causing it to produce a substantially larger embryo or germ than it would otherwise had it been pollinated by plants other than TC Blend® pollinators. These TC Blend® pollinators are also sufficiently heterogeneous in the timing of flowering that obtaining synchrony of flowering between the TC Blends pollinator and the TC Blend® grain parent under field conditions is very often well predicted from small research trials.

However, there are limitations to many of these current TC Blend® pollinators. Some individual TC Blend® pollinators demonstrate less potential for vegetative development than the TC Blend® grain parent with which they are paired. As a result, the TC Blend® pollinator plants will be unable to secure sufficient light, soil moisture and mineral nutrients due to its being surrounded by larger and more vigorous TC Blend® grain parents. This will result in the TC Blend® pollinator plants not achieving their genetic potential. This lack of competitive ability can be exacerbated under conditions of environmental stress. For example, under drought stress, some current TC Blend® pollinators may be less able to extract soil moisture and/or to survive on reduced soil moisture than the TC Blend® grain parent with which it is blended. As a result, the ability of the TC Blend® pollinator to shed sufficient pollen may be adversely affected and/or there may be a significant change in the time when it would shed pollen. Furthermore, the ability of the seed of some current TC Blend® pollinators to maintain acceptable vigor over time in storage is less than desirable due to the fact that the plant on which the seed is grown is generally weak and prone to disease. As a result, the yield of high quality seed of these TC Blend® pollinators may be limited. Thus, there exists a need for a class of TC Blend® pollinators that demonstrate considerably more vegetative vigor and environmental durability and produce higher quality seed than what is generally available.

Another limitation of many existing TC Blend® pollinators used in the TopCross® system is their restriction to a narrow geographic range. The current types of TC Blend® pollinators, both the synthetics and synthetic hybrids, cannot currently be paired with all possible TC Blend® grain parents. Silk extrusion by some TC Blend® grain parents may be either too early or too late to be synchronous with pollen shed by these TC Blend® pollinators.

SUMMARY OF THE INVENTION

Applicants have discovered a type of high-oil pollinator with enhanced vegetative vigor and environmental durability, greater range in the timing of pollen shed, and broader geographic adaptability. The instant invention pertains to a 3:1 grain production high oil pollinator comprising the progeny of the cross of a corn primary hybrid, said corn primary hybrid derived from the cross of a corn inbred and a first high oil source, and a second high oil source, said first and second high oil sources selected from the group of consisting of P20, ASKC28, P22, P58, UHOC3-51, P39 and P39A, wherein said first high oil source and second high oil source are the same or different. Another embodiment of the instant invention is the seed derived from the 3:1 grain production high oil pollinator corn plant.

Yet another embodiment of the instant invention is a method for producing 3:1 grain production high oil pollinator corn seed which produces the instant 3:1 grain production high oil pollinator corn plant comprising the following steps: (a) planting in pollinating proximity seed of a corn inbred and seed of a first high oil source to obtain corn plants, wherein either the corn inbred or the first high oil source has been rendered male sterile prior to pollination; (b) permitting natural cross pollination to occur between the corn inbred and the first high oil source; (c) harvesting the resulting seed produced on the male sterile plant to obtain corn primary hybrid seed; (d) planting in pollinating proximity the corn primary hybrid seed and seed of a second high oil source to obtain corn plants, wherein either the corn primary hybrid or the second high oil population has been rendered male sterile prior to pollination; (e) permitting natural cross pollination to occur between the corn primary hybrid and the second high oil source; and (f) harvesting the resulting seed produced on the male sterile plant to obtain 3:1 grain production high oil pollinator seed; wherein the first and second high oil sources are selected from the group of consisting of P20, ASKC28, P22, UHOC3-51, P39, P39A and P58, and wherein the first high oil source and the second high oil source are the same or different.

BIOLOGICAL DEPOSITS

The following high oil sources have been deposited under the terms of the Budapest Treaty at American Type Culture Collection (ATCC), 12301 Parklawn Drive, Rockville, Md. 20852, and bear the following accession numbers:

| High Oil Source | Accession Number | Date of Deposit |
| --- | --- | --- |
| P20 | ATCC 97872 | February 20, 1997 |
| ASKC28 | ATCC 75105 | September 19, 1991 |
| P22 | ATCC 97871 | February 20, 1997 |
| P39 | ATCC 97023 | January 23, 1995 |
| P39A | ATCC 97696 | September 5, 1996 |

-continued

| High Oil Source | Accession Number | Date of Deposit |
|---|---|---|
| P58 UHOC3-51 | ATCC 97868 | February 20, 1997 |

DETAILED DESCRIPTION OF THE INVENTION

In the context of this disclosure, a number of terms shall be used.

The term "corn" refers to any variety, cultivar or population of Zea mays L. "Field corn" refers to varieties or cultivars of corn grown extensively on large acreages within a broad but defined geographic area for the production of grain and/or forage. Most field corn in the United States is also referred to as "dent" corn, whereas field corn produced in Europe and Argentina is more likely to be referred to as "flint" or "flint-dent" corn. The phrase "high oil corn" refers to corn plants, hybrids, varieties, lines, populations, synthetics or synthetic hybrids that produce corn kernels that contain oil at elevated concentrations when compared to corn kernels produced by corn plants, hybrids, varieties, lines, populations, synthetics or synthetic hybrids other than high oil corn. "High oil corn" also refers to the kernels or grain itself. A "high oil source" is a corn plant, hybrid, variety, line, population, synthetic or synthetic hybrid used as a source of high oil genes. Corn kernels produced by a high oil source contain oil at elevated concentrations when compared to corn kernels produced by a non-high oil sources.

The terms "variety" or "cultivar" refer to a group of similar plants that by structural features and performance can be identified from other varieties or cultivars within the same species. The term "line" refers to a group of individuals from a common ancestry; a more narrowly defined group than a variety. A "synthetic" or "synthetic population" is a genetically heterogeneous collection of plants of known ancestry created by the intermating of any combination of inbreds. hybrids, varieties, populations, races or other synthetics. The term "population" refers to a genetically heterogeneous collection of plants sharing a common genetic derivation. A "synthetic hybrid" is an F1 hybrid between two different synthetics.

The term "inbred" refers to a substantially homozygous individual, variety or line. The term "hybrid" refers to any offspring of a cross between two genetically unlike individuals (see Rieger R., et al. A Glossary of Genetics and Cytogenetics; Springer-Verlag: New York, 1968).

The term "seed" refers to the mature corn kernel produced for the purpose of propagating the species and it is commonly sold to grain producers. "Germ" is the embryo of the corn kernel and contains most of the oil found in the kernel. A "kernel" is the corn caryopsis, comprising in part a mature embryo and an endosperm which are products of double fertilization. A kernel is also the corn fruit. An "ovule" is a structure consisting of female reproductive tissue surrounded by maternal tissue. During the development of a corn plant the ovule will eventually contain a haploid egg nucleus and two haploid polar nuclei. The ovule will develop into a mature corn kernel following fusion with sperm nuclei found in pollen. "Pollen" is a structure which ultimately contains the two haploid sperm nuclei which fuse with the egg nucleus and polar nuclei found in the ovule to give rise to the embryo and endosperm of the mature corn kernel.

The term "grain" comprises mature corn kernels produced by growers for on-farm use or for sale to customers, in both cases for purposes other than growing or reproducing the species. Typical customers would include but not be limited to livestock feeders, wet or dry millers or animal feed formulators. "Grain parent" refers to a male sterile hybrid that comprises a large majority of the plants in a field used in the T TopCross® grain production system. Typically, the percentage of grain parent seed in a TC Blend seed corn product is between 90 and 92%. "Grain parent seed" refers to corn seed that when sown germinates to produce grain parent plants. A "seed parent" is an inbred corn line or a hybrid corn line that is pollinated by pollen from pollinator plants, with the seed resulting from this pollination being produced on the seed parent. This seed comprises hybrid corn seed. A "male sterile" plant is a plant that fails to produce functional pollen as a consequence of mechanical or hand detasseling, incorporation of genetic or cytoplasmic sterility, or by some other mechanism.

The term "homozygous" refers to a genetic condition existing when identical alleles reside at corresponding loci on homologous chromosomes. The term "heterozygous" refers to a genetic condition existing when different alleles reside at corresponding loci on homologous chromosomes.

A "pollinator" is a corn plant or group of corn plants (e.g., a variety, hybrid, line, population, synthetic or synthetic hybrid) whose principal function is to shed pollen within a corn field. "Pollinator seed" refers to corn seed that when sown germinates to produce pollinator plants.

An "enhanced quality grain trait" is a grain trait which is statistically different in quantity from that found in field corn grain obtained from self pollination of a fertile version of the female corn plant. Enhancement may involve either an increase in a property or characteristic deemed advantageous resulting in a higher amount or level of the quality grain trait or a decrease in a property or characteristic deemed detrimental resulting in a lower amount or level of the quality grain trait.

The term "percent (%) oil" refers to the oil concentration of a corn kernel expressed on a dry weight basis. The phrase "general combining ability" refers to the average or overall performance of a genetic strain in a series of crosses. "Specific combining ability" is the performance of specific combinations of genetic strains in crosses in relation to the average performance of all combinations.

The term "TC Blend®" refers to a mixture of plants consisting of a pollinator and a grain parent used in the TopCross® grain production system. A "TC Blend® grain parent" is a grain parent plant or hybrid used in the TopCross® grain production system to produce grain. A "TC Blend® pollinator" is a pollinator plant, hybrid, variety, line, population, synthetic or synthetic hybrid that is used in the TopCross® grain production system primarily to produce pollen. "TC Blend® pollinator seed" is corn seed that when sown germinates to produce TC Blend® pollinator plants. "TC Blend® seed corn" is a mixture of TC Blend® pollinator seed and grain parent seed that when sown germinate to produce TC Blend® pollinator plants and grain parent plants used in the TopCross®b grain production system.

The phrase "TopCross® grain production system" refers to a method of corn production resulting from the sowing of TC Blend® seed corn. Pollination of the TC Blend® grain parent by the TC Blend® pollinator changes the chemical composition of the grain produced by the TC Blend® grain parent. This change includes but is not limited to an increase in oil concentration. "TopCross® grain" is corn grain produced in the TopCross® grain production system.

The term "3:1 grain production high oil pollinator" refers to corn plants or a group of corn plants (e.g., a variety, hybrid, line, population, synthetic or synthetic hybrid) whose principal function is to shed pollen within a corn field derived from TC Blend® seed corn. "3:1 grain production high oil pollinator corn seed" is corn seed that when sown germinates to produce 3:1 grain production high oil pollinator plants. 3:1 grain production high oil pollinator corn seed is produced by fertilizing the stigmata of the progeny of a cross of an inbred corn line and a high oil source line with the pollen from a high oil source line.

The method of production of 3:1 grain production high oil pollinators may be represented as:

(inbred x high oil source) x high oil source

The first or primary cross (inbred x high oil source) is an F1 hybrid, referred to as the primary hybrid. Either plant, the inbred or the high oil source, may be used as either the seed parent or the pollinator in the primary cross. Upon sowing seed of the primary hybrid, the silks of the resulting hybrid plant are, in turn, pollinated by pollen from a second high oil source. This is the secondary cross. Seed produced as a result of the secondary cross is 3:1 grain production high oil pollinator corn seed, and by parentage, seventy-five percent of the genome of 3:1 grain production high oil pollinators is derived from high oil sources and 25% is derived from inbred lines. 3:1 grain production high oil pollinator corn seed is mechanically mixed with TC Blend® grain parent seed to produce TC Blend® corn seed. TC Blend® corn seed is sown in order to produce TopCross® grain, which has more value per bushel than corn not containing enhanced grain quality traits.

The present invention provides a specific class of corn plants that is better adapted to serve as TC Blend® pollinators in TopCross® grain production than many of the TC Blend® pollinators currently in use. Members of this inventive class of TC Blend® pollinators, known as 3:1 grain production high oil pollinators, are better able to compete vegetatively with TC Blend® grain parents with which they are paired, improving their ability to perform under conditions of environmental stress. Even under ideal environmental conditions, the inventive 3:1 grain production high oil pollinators are expected to shed more pollen per plant than many of the current TC Blend® pollinators, thus allowing for greater range in blending options of TC Blend® pollinator with TC Blend® grain parent seed. Use of the instant 3:1 grain production high oil pollinators also improves the yields of high quality TC Blend® pollinator seed as well as the ability of this seed to maintain vigor over time in storage. Furthermore, the means whereby lines are combined genetically to produce this class of corn plants allows for a very rapid means for developing numerous TC Blend® pollinators representing a wide range of maturities. As a result, TC Blend® grain parents that do not flower at the same time as the current TC Blend® pollinators can be now be used very effectively in TopCross® grain production, thus greatly broadening both the geographic range and the genetic breadth of this technology.

The specific inbreds used in the production of 3:1 grain production high oil pollinators are not at all critical and, therefore, can readily represent a broad range of maturities and, thus, germplasm. The broad range of maturities of inbreds available to seed companies is one of the fundamental reasons for the benefits of 3:1 grain production high oil pollinators; i.e., their ability to cover a wide range of environments. The inbreds useful in producing 3:1 grain production high oil pollinators include inbreds adapted not only to all portions of the corn growing areas of the U.S., but also corn growing regions outside of the U.S. For instance, use of inbreds including but not limited to those adapted to the northern U.S. corn belt as well as European inbreds will enable the production of extremely early 3:1 grain production high oil pollinators that will best serve the needs of the northern U.S. corn belt (e.g., North Dakota, South Dakota, Minnesota, Wisconsin, Michigan, Pennsylvania, New York, etc.). At the other extreme, use of inbreds including but not limited to those adapted to the southern U.S. corn belt as well as South American inbreds will enable the production of extremely late 3:1 grain production high oil pollinators that will best serve the needs of the southern U.S. corn belt (e.g., Kansas, Missouri, southern Illinois, southern Indiana, Kentucky, the Delmarva peninsula, etc.). Furthermore, inbreds that have slightly elevated oil levels (e.g., LH82, LH172) would be well adapted for use in producing 3:1 grain production high oil pollinators since they will contribute to the xenia effect in the elevation of oil in TopCross® Grain. Inbred lines, including but not limited to those in Table 1, below, may be utilized and are herein incorporated by reference.

TABLE 1

| Inbred | U.S. Pat. No. | Inbred | U.S. Pat. No. |
| --- | --- | --- | --- |
| LH189 | 5,545,811 | PHTE4 | 5,495,069 |
| LH231 | 5,495,068 | PHW06 | 5,495,065 |
| LH252 | 5,495,067 | PHKM5 | 5,491,286 |
| LH176 | 5,491,296 | PHR61 | 5,463,173 |
| LH185 | 5,491,294 | PHTE4 | 5,453,564 |
| LH225 | 5,491,293 | PHHB4 | 5,444,178 |
| LH168 | 5,457,275 | PHR03 | 5,436,390 |
| LH169 | 5,436,388 | PHT11 | 5,343,346 |
| LH218 | 5,436,387 | PHRE1 | 5,416,254 |
| LH186 | 5,416,262 | PHFA5 | 5,387,755 |
| LH185 | 5,416,261 | PHGW7 | 5,387,754 |
| LH225 | 5,416,255 | PHHB9 | 5,367,109 |
| LH211 | 5,387,743 | PHMKO | 5,365,014 |
| LH217 | 5,304,727 | PHEM9 | 5,354,942 |
| LH167 | 5,304,726 | PHEW7 | 5,354,941 |
| LH198 | 5,304,717 | PHTM9 | 5,349,119 |
| LH197 | 5,304,716 | PHK56 | 5,347,081 |
| LH199 | 5,304,715 | PHK74 | 5,347,080 |
| LH164 | 5,304,714 | PHGV6 | 5,347,079 |
| LH181 | 5,304,713 | PHHV4 | 5,304,720 |
| LH206 | 5,304,712 | PHT47 | 5,304,719 |
| LH200 | 5,285,005 | PHBW8 | 5,285,004 |
| LH204 | 5,285,003 | PHR31 | 5,276,265 |
| LH163 | 5,285,001 | PHJ90 | 5,245,125 |
| LH159 | 5,276,267 | PHJ65 | 5,220,114 |
| LH172 | 5,276,266 | PHP55 | 5,159,134 |
| LH216 | 5,276,263 | PHV37 | 5,159,133 |
| LH210 | 5,276,262 | PHR63 | 5,159,132 |
| LH212 | 5,276,260 | PHN73 | 5,157,208 |
| LH213 | 5,276,259 | PHN82 | 5,157,206 |
| LH195 | 5,059,745 | PHW20 | 5,097,096 |
| phte4 | 5,569,822 | PHM10 | 5,097,095 |
| PHT11 | 5,569,821 | PHP60 | 5,097,094 |
| PHN46 | 5,567,861 | PHJ33 | 5,097,093 |
| PHN18 | 5,557,034 | PHR62 | 5,097,092 |
| PHRF5 | 5,545,813 | PHK35 | 5,095,174 |
| PHK46 | 5,543,575 | PHP02 | 5,082,992 |
| PHRD6 | 5,541,352 | PHN37 | 5,082,991 |
| PHAP1 | 5,530,184 | PHK29 | 4,812,600 |
| PHTD5 | 5,527,986 | PHV78 | 4,812,599 |
| PHN82 | 5,506,368 | PHK05 | 4,806,669 |
| PHP38 | 5,506,367 | PHR25 | 4,806,652 |

EXAMPLE 1

3:1 grain production high oil pollinators are, as a class, larger, more vigorous, better able to shed pollen under a wider range of environmental conditions, and better able to compete with larger TC Blend® grain parents than many of the synthetic and synthetic hybrid TC Blend® pollinators currently in use. 3:1 grain production high oil pollinators demonstrate superior plant stature, as exemplified by greater plant and ear height, than do many of the synthetics and hybrid synthetics in use today as TC Blend® pollinators.

In 1995, the seed yields and plant stature of two different examples of 3:1 grain production high oil pollinators were compared to the seed yields and plant statures of four different synthetics in field trials. Seed yields summmnarized in Table 2 were measured in El Paso, Ill.; Oakford, Ill.; Pesotum, Ill.; and Newburgh, Ind. There were three replicates at each location, each replicate containing one plot. Each plot consisted of two 30-inch rows, each 20 feet long. All plots were sown between April 25 and May 6. Seed yield data in this table represents the mean yields across replicates and locations. Of the four high oil sources in these trials, three are currently in use as TC Blend® pollinators. The last of the four, P58, is a candidate for adoption. At only the El Paso location, plant and ear heights were also measured. Three measurements of both heights were made within one plot and averaged together. These data are also included in Table 2.

TABLE 2

Average seed yield, plant height and ear height of two examples of 3:1 grain production high oil pollinators and four high oil sources in 1995 field trials. Seed yield of each pollinator was the mean production from four different locations. Plant and ear heights were the means of three measurements from one plot in El Paso, Illinois.

| Pollinator | Seed Yield of Pollinator (bu/acre) | Plant Height (cm) |
| --- | --- | --- |
| 3:1 grain production high oil pollinators | | |
| (LH195 × P20) × ASKC28 | 71.1 | 229 |
| (LH150 × P22) × ASKC28 | 58.5 | 244 |
| Mean | 64.8 | 237 |
| High Oil Sources | | |
| P20 | 39.6 | 221 |
| ASKC28 | 38.4 | 244 |
| P22 | 37.2 | 221 |
| P58 | 36.8 | 190 |
| Mean | 38.0 | 219 |

The mean seed yield of the two 3:1 grain production high oil pollinators was 64.8 bushels per acre, over 70% greater than the mean seed yield of the high oil sources. The mean plant height of the two 3:1 grain production high oil pollinators was 237 cm, over 8% greater than the mean height of the high oil sources.

EXAMPLE 2

In 1995, the plant stature and vigor of 21 different 3:1 grain production high oil pollinators were compared to the plant stature and vigor of two different synthetics currently in use as TC Blend® pollinators in a nursery field trial in El Paso, Ill. Five plants chosen randomly from a single 30-inch wide, 20-ft long row were measured for plant height and scored for tassel size and vigor on a scale of from 1 as the least vigorous to 5 as the most vigorous. The results are summarized in Table 3.

TABLE 3

Average plant height, tassel size score and plant vigor score of 21 different 3:1 grain production high oil pollinators and two synthetics in 1995, at El Paso, Illinois, in a nursery field trial consisting of single row plots, each 30 inches wide and 20 feet long. Data represent the means of individual measurements of five randomly selected plants within each plot.

| Pollinator | Plant Height (cm) | Tassel Size * | Plant Vigor * |
| --- | --- | --- | --- |
| 3:1 grain production high oil pollinators: | | | |
| (ASKC28 × LH252) × P20 | 152 | 4.0 | 4.0 |
| (ASKC28 × LH252) × P22 | 184 | 4.0 | 4.0 |
| (LH150 × P20) × ASKC28 | 198 | 4.0 | 4.0 |
| (LH150 × P22) × ASKC28 | 204 | 4.0 | 2.5 |
| (LH188 × P20) × ASKC28 | 175 | 4.0 | 4.0 |
| (LH188 × P22) × ASKC28 | 198 | 3.5 | 3.0 |
| (LH195 × P20) × ASKC28 | 192 | 4.0 | 3.5 |
| (LH195 × P22) × ASKC28 | 183 | 4.0 | 4.0 |
| (LH195 × P22) × P39 | 160 | 4.0 | 3.0 |
| (LH219 × P20) × ASKC28 | 183 | 4.0 | 4.0 |
| (LH219 × P22) × ASKC28 | 152 | 4.0 | 3.0 |
| (LH260 × ASKC28) × P39 | 168 | 4.0 | 3.0 |
| (LH260 × ASKC28) × P22 | 168 | 4.0 | 4.0 |
| (P39A × LH123) × ASKC28 | 175 | 4.0 | 4.0 |
| (P39A × LH123) × P22 | 168 | 4.0 | 3.0 |
| (LP46 × P20) × ASKC28 | 206 | 4.0 | 4.0 |
| (LP46 × P22) × ASKC28 | 198 | 4.0 | 4.0 |
| (NC286 × P22) × ASKC28 | 160 | 3.0 | 4.0 |
| (NC286 × P20) × ASKC28 | 168 | 4.0 | 3.0 |
| (NC286 × P20) × P39 | 198 | 4.0 | 3.0 |
| (NC286 × P22) × ASKC28 | 168 | 3.0 | 3.0 |
| Mean | 179 | 3.9 | 3.5 |
| High Oil Sources: | | | |
| ASKC28 | 175 | 3.0 | 2.0 |
| P22 | 159 | 3.0 | 2.0 |
| Mean | 167 | 3.0 | 2.0 |

* Rating scale: 1 to 5 = Lesser to Greater

Mean plant height of all the 3:1 grain production high oil pollinators was 179 cm, 7% greater than the mean plant height of the two current TC Blend® pollinators. Tassel size score averaged 3.9 for the 3:1 grain production high oil pollinators, 30% greater than the mean of the two current TC Blend® pollinators. Mean plant vigor scored was 3.5 for the 3:1 grain production high oil pollinators, 75% greater than the mean of the two current TC Blend® pollinators.

The greater plant stature and improved plant vigor demonstrated by 3:1 grain production high oil pollinators when compared to high oil sources as TC Blend® pollinators under similar field conditions indicates that more TC Blend® pollinators may be developed from this class of plants that will be better suited to compete with hybrid TC Blend® grain parents.

EXAMPLE 3

As evidence of superior performance of 3:1 grain production high oil pollinators when used as TC Blend® pollinators, mean yields of TopCross® grain across three locations in 1994 were to the yield of the fertile version of the Grain Parent (Table 4). In these trials, a single 3:1 grain production high oil pollinator was combined with three different grain parents in three separate TC Blend® seed corn products. Each was tested at three locations. The three locations were Macomb and Ridgeway, Ill., and Remington, Ind. There was one replication at each location. In Ridgeway, Ill., yield data were collected from 8-row plots, each 20 feet wide and 50 feet long. In Remington, Ind., and Macomb, Ill., yield data were collected from 8-row plots, each 20 feet wide and 100 feet long. Grain samples at least ½ pound in size were collected from oil analyses at the DuPont Quality Grains Research and Development Center in Des Moines, Iowa. Oil analyses were performed using near infrared transmittance spectroscopy.

TABLE 4

Average TopCross ® grain yield per acre and oil levels in that grain of several TC Blend ® seed corn products with a 3:1 grain production high oil pollinator produced in Macomb and Ridgeway, Illinois, and Remington, Indiana, in 1994.

| TC Blend ® Grain Parent + Pollinator | Grain Yield per Acre at 15% Moisture | | Oil Level in Grain |
|---|---|---|---|
| | (bu/acre) | (% of Grain Parent Check) | (%; at 0% moisture) |
| A + (LH192 × UHOC3-51) × ASKC28 | 155.8 | 85.0% | 7.3% |
| B + (LH192 × UHOC3-51) × ASKC28 | 161.7 | 93.0% | 8.4% |
| C + (LH192 × UHOC3-51) × ASKC28 | 169.0 | 92.0% | 6.8% |
| Means | 162.2 | 90.0% | 7.5% |

The mean TopCross® grain yield with this 3:1 grain production high oil pollinator was 162.2 bushels per acre across all three grain parents. Oil levels averaged 7.5% across all three TC Blend® seed corn products. This pollinator exemplified improved vigor and pollen shed in all these trials.

EXAMPLE 4

As further evidence of superior performance of 3:1 grain production high oil pollinators when used as TC Blend® pollinators, mean yields of TopCross® grain across four locations in 1995 were compared to the yield of TopCross® grain from a TC Blend® in which a high oil source was used as a TC Blend® pollinator (Table 3). The four locations were Champaign and Mason City, Ill., Noblesville, Ind., and Oran, Mo. There was one replication at each location. In Champaign, Mason City and Noblesville, yield data were collected from 8-row plots, each 24 feet wide and at least 100 feet long. In Oran, yield data were collected from 12-row plots, 30 feet wide and at least 100 feet long. Grain samples at least ½ pound in size were collected for oil analyses at the DuPont Quality Grains Research and Development Center in Des Moines, Iowa. Oil analyses were performed using near infrared transmittance spectroscopy.

TABLE 5

Average TopCross ® grain yield per acre and oil levels in that grain of several TC Blend ® seed corn products with either an high oil source pollinator or one of three different 3:1 grain production high oil pollinators.

| TC Blend ® Grain Parent + Pollinator | Grain Yield per Acre at 15% Moisture | | | Oil Level in Grain |
|---|---|---|---|---|
| | (bu/acre) | (% of Grain Parent Check) | (% of Grower's Check) | (%; at 0% moisture) |
| A + P22 | 118.2 | 93.3% | 96.4% | 6.7% |
| 3:1 grain production high oil pollinators: | | | | |
| A + (LH150 × P22) × ASKC28 | 124.2 | 96.0% | 110.7% | 7.1% |
| A + (LH195 × P20) × ASKC28 | 125.8 | 97.9% | 107.2% | 6.8% |
| A + (ASKC28 × LH252) × P22 | 143.0 | 110.0% | 114.2% | 6.7% |
| Means | 131.0 | 101.3% | 110.7% | 6.9% |

Mean TopCross® grain yield with 3:1 grain production high oil pollinators was 131.0 bushels per acre, nearly 11% greater than the grain yield with the high oil source pollinator. Grain yields ranged from as little as 5% greater to as much as 21% greater. Furthermore, TopCross® grain yields were greater on average than was the grain yield of the "grain parent check" (the grain parent check was a male-fertile version of the TC Blend® grain parent, A). Grain yields were also greater on average with each 3:1 grain production high oil pollinator in the TC Blend® than was the grain yield of a typical hybrid chosen by the grower (i.e., the "grower's check"). Oil levels were equal to or better when using the 3:1 grain production high oil pollinators than when using the high oil source.

EXAMPLE 5

Since the genotype of 3:1 grain production high oil pollinators calls for the inclusion of one inbred, it is possible to use an inbred that has a markedly different time of flowering to alter quickly the flowering date. As a result, it is possible to produce TC Blend® pollinators that have a different flowering date than the component high oil sources. Thus, TC Blend® grain parents can be used in TC Blend® seed corn that would otherwise not be possible. Observations on flowering dates were made in El Paso, Ill., in 1995, in a nursery field trial consisting of single 30-inch wide, 20-ft long rows. Observations were made of the entire row as a unit. Differences in days until 50% of the plants within the plot were at anthesis (i.e., pollen shed) were recorded among several examples of 3:1 grain production high oil pollinators and compared to two high oil sources. These data are in Table 6.

TABLE 6

Average number of days until half of the plants within a row are at anthesis of several examples of 3:1 grain production high oil pollinators and two high oil sources. Observations were made in a single plot consisting of a single row, 30 inches wide and 20 feet long.

| Pollinator | Days to 50% Anthesis |
|---|---|
| 3:1 grain production high oil pollinators | |
| (ASKC28 × LH252) × P20 | 82 |
| (ASKC28 × LH252) × P22 | 82 |
| (LH195 × P22) × P39 | 81 |
| (LH260 × ASKC28) × P39 | 81 |
| (NC286 × P20) × P39 | 81 |
| (LH150 × P20) × ASKC28 | 79 |
| (LH150 × P22) × ASKC28 | 78 |
| (LH195 × P20) × ASKC28 | 76 |
| (LH195 × P22) × ASKC28 | 76 |

TABLE 6-continued

Average number of days until half of the plants within a row are at anthesis of several examples of 3:1 grain production high oil pollinators and two high oil sources. Observations were made in a single plot consisting of a single row, 30 inches wide and 20 feet long.

| Pollinator | Days to 50% Anthesis |
| --- | --- |
| (LH219 × P22) × ASKC28 | 76 |
| (LH260 × ASKC28) × P22 | 76 |
| (LH39A × LH123) × ASKC28 | 76 |
| (NC286 × P20) × ASKC28 | 76 |
| (LH188 × P20) × ASKC28 | 75 |
| (LH188 × P22) × ASKC28 | 74 |
| (LH219 × P20) × ASKC28 | 74 |
| (P39A × LH123) × P22 | 74 |
| (P46 × P20) × ASKC28 | 74 |
| (P46 × P22) × ASKC28 | 74 |
| (NC286 × P20) × ASKC28 | 73 |
| (NC286 × P22) × ASKC28 | 73 |
| *Mean* | *77* |
| High Oil Source | |
| ASKC28 | 74 |
| P22 | 73 |
| *Mean* | *75* |

Therefore, the two high oil sources in Table 6, ASKC28 and P22, differ only slightly from each other in their times until 50% anthesis. However, inclusion of a variety of inbred lines with varying maturities enables the production of many 3:1 grain production high oil pollinators that achieve 50% anthesis over a much wider range: from as early as 73 to as late as 82 days after planting. This enables the use of a much wider range of hybrid corn varieties as TC Blend® grain parents in TopCross® grain production.

EXAMPLE 6

Oil levels produced by a wide range of hybrids when pollinated by 3:1 grain production high oil pollinators are greater than oil levels when those same hybrids pollinate themselves ("self" pollinations). This is demonstrated in Table 7. The data here were collected in 1995, from pollinations made by hand using bulked pollen. Plots consisted of a single 30-inch row, 20 feet long, in El Paso, Ill. At least 10 pollinations were made to produce at least six ears over approximately 10 days. Grain from these ears was analyzed for oil level by near infrared transmittance spectroscopy at the DuPont Quality Grains Research and Development Center in Des Moines, Iowa. The results in Table 6 compare the oil levels in TopCross® grain produced by two different 3:1 grain production high oil pollinators when used to pollinate 32 different hybrids versus self pollinations by these same hybrids. Additionally, TopCross® grain produced in this same trial when two high oil sources were used as TC Blend® pollinators were also analyzed and the data included in Table 7.

TABLE 7

Oil concentration in grain produced by self pollination of 32 different male fertile hybrids in comparison to the oil concentration in grain produced by the pollination of male sterile versions of those same hybrids by two examples of 3:1 grain production high oil pollinators. Data were collected from at least 10 hand-pollinations, producing approximately six ears per hybrid/pollinator combination in nursery trials in El Paso, Illinois, in 1995.

| | Oil Concentration in Grain Resulting from Pollination by: | | |
| --- | --- | --- | --- |
| Hybrid | Self | (LH150 × P22) × ASKC28 | (LH195 × P20) × ASKC28 |
| | | (% oil at 0% moisture) | |
| 2375 | 4.5 | 9.2 | 6.8 |
| 1571 | 4.7 | 9.0 | 10.1 |
| 2020 | 3.9 | 8.9 | 7.7 |
| 3001 | 4.5 | 8.4 | 11.5 |
| 2675 | 4.2 | 8.3 | 7.4 |
| 2640 | 4.9 | 8.3 | 7.9 |
| X632 | 4.7 | 8.2 | 7.6 |
| X642 | 4.2 | 8.2 | 8.1 |
| 3034 | 4.3 | 8.2 | 10.7 |
| X528 | 5.0 | 8.1 | 9.8 |
| 2320 | 4.7 | 8.1 | 7.9 |
| X571 | 3.6 | 8.0 | 9.2 |
| X591 | 4.6 | 8.0 | 8.5 |
| 2680 | 4.6 | 7.9 | # |
| X601 | 4.6 | 7.9 | 6.5 |
| 3225 | 4.1 | 7.9 | 7.1 |
| X577 | 4.4 | 7.9 | 8.4 |
| 2010 | 4.3 | 7.7 | 8.3 |
| X636 | 4.9 | 7.7 | 8.0 |
| 2652 | 4.2 | 7.7 | 7.6 |
| 2417 | 4.6 | 7.6 | 7.6 |
| X641 | 4.4 | 7.5 | 7.5 |
| X595 | 4.7 | 7.4 | 7.1 |
| X631 | 3.5 | 7.4 | # |
| 2650 | 3.9 | 7.3 | 6.5 |
| 3333 | 3.7 | 7.3 | 7.7 |
| X633 | 4.5 | 7.2 | 8.1 |
| X570 | 3.4 | 7.2 | 6.9 |
| 3434 | 4.2 | 7.2 | 7.8 |
| X637 | 4.3 | 6.8 | 7.0 |
| X592 | 4.3 | 6.6 | 7.3 |
| X634 | 4.0 | 6.6 | 6.4 |
| *Mean* | *4.3* | *7.8* | *8.0* |

No pollinations made.

Oil levels in the TopCross® grain averaged 7.8% and 8.0% across 32 different hybrids used as grain parents when pollinated by two examples of 3:1 grain production high oil pollinators. These levels, respectively, 81% and 86% higher than the average oil level in the grain produced on those same hybrids by self pollination.

EXAMPLE 7

Inclusion of a range of inbreds in the production of TC Blend® pollinators can be accomplished while at the same time generating TC Blend® pollinators that can significantly alter the chemical composition of TopCross® grain. Grain samples produced on several TC Blend® grain parents from a range of 3:1 grain production high oil pollinators were analyzed for oil concentration. Pollinations were made by hand, using bulked pollen. Plots consisted of a single 30-inch row, 20 feet long. At least 10 pollinations were made to produce at least six ears over approximately 10 days. Grain from these ears was analyzed for oil level by near infrared transmittance spectroscopy at the DuPont Quality Grains Research and Development Center in Des Moines, Iowa. The results in Table 7 compare the oil levels in TopCross® grain produced by three hybrid corn varieties when pollinated by 21 different 3:1 grain production high oil pollinators to TopCross® grain produced by two high oil sources.

TABLE 8

Oil concentration in grain produced by pollination of three hybrid corn varieties by 21 different 3:1 grain production high oil pollinators in comparison to pollination of the same three hybrid corn varieties by two high oil sources. Data were collected from at least 10 hand-pollinations, producing approximately six ears per hybrid/pollinator combination in nursery trials in El Paso, Illinois, in 1995.

| Pollinator | Hybrid Corn Varieties | | | |
|---|---|---|---|---|
| | X577 | 3333 | X595 | Mean |
| | (% oil at 0% moisture) | | | |
| 3:1 grain production high oil pollinators | | | | |
| (LH195 × P22) × ASKC28 | 7.7 | 7.2 | 7.5 | 7.5 |
| (LH150 × P20) × ASKC28 | 7.9 | 7.1 | 7.4 | 7.5 |
| (LH150 × P22) × ASKC28 | 7.8 | 7.1 | 7.3 | 7.4 |
| (LH219 × P22) × ASKC28 | 7.8 | 7.0 | 7.2 | 7.3 |
| (NC286 × P20) × ASKC28 | 7.9 | 6.8 | 7.2 | 7.3 |
| (NC286 × P22) × ASKC28 | 7.1 | 7.3 | 7.2 | 7.2 |
| (LH219 × P20) × ASKC28 | 7.2 | 7.0 | 7.1 | 7.1 |
| (LH188 × P22) × ASKC28 | 7.5 | 7.0 | 6.6 | 7.0 |
| (P46 × P20) × ASKC28 | 7.3 | 6.4 | 7.1 | 6.9 |
| (LH195 × P20) × ASKC28 | 7.1 | 6.8 | 7.0 | 6.9 |
| (LH188 × P20) × ASKC28 | 7.1 | 6.4 | 7.0 | 6.9 |
| (P46 × P22) × ASKC28 | 7.1 | 6.6 | 6.6 | 6.8 |
| (ASKC28 × LH252) × P22 | 7.3 | 6.5 | 6.5 | 6.8 |
| (NC286 × P20) × ASKC28 | 6.8 | 6.5 | 6.8 | 6.7 |
| (P39A × LH123) × ASKC28 | 7.2 | 6.4 | 6.5 | 6.7 |
| (LH195 × P22) × P39 | 6.6 | 6.5 | 6.5 | 6.6 |
| (LR260 × ASKC28) × P39 | 6.8 | 6.2 | 6.6 | 6.5 |
| (NC286 × P20) × P39 | 7.1 | 6.1 | 6.4 | 6.5 |
| (LH260 × ASKC28) × P22 | 7.2 | 5.8 | 6.1 | 6.4 |
| (ASKC28 × LH252) × P20 | 6.7 | 6.0 | 6.3 | 6.3 |
| (P39A × LH123) × P22 | 6.3 | 5.7 | 5.9 | 6.0 |
| High Oil Sources | | | | |
| ASKC28 | 9.3 | 9.1 | 8.5 | 9.0 |
| P22 | 7.6 | 7.2 | 7.3 | 7.4 |

In Table 8, many different 3:1 grain production high oil pollinators produced oil levels in TopCross® grain similar to that produced via the P22 high oil source. Thus, 3:1 grain production high oil pollinators can produce TopCross® grain with oil concentrations similar to those produced via high oil sources.

What is claimed is:

1. A 3:1 grain production high oil pollinator comprising the progeny of the cross of a corn primary hybrid, said corn primary hybrid derived from the cross of a corn inbred and a first high oil source, and a second high oil source, said first and second high oil sources selected from the group consisting of P20 having ATCC Accession No. 97872, ASKC28 having ATCC Accession No. 75105, P22 having ATCC Accession No. 97871, P58 having ATCC Accession No. 97868, UHOC3-51 having ATCC Accession No. 97969, P39 having ATCC Accession No. 97023 and P39A having ATCC Accession No. 97696, wherein said first high oil source and second high oil source are different.

2. A 3:1 grain production high oil pollinator of claim 1 wherein said first high oil source and said second high oil source are the same.

3. Seed derived from the 3:1 grain production high oil pollinator of claim 1 or 2.

4. A method for producing a 3:1 grain production high oil pollinator seed which produces a 3:1 high oil pollinator plant capable of serving as a high oil pollinator, comprising the steps of:

(a) planting in pollinating proximity seed of a corn inbred and seed of a first high oil source to obtain corn plants, wherein either the corn inbred or the first high oil source has been rendered male sterile prior to pollination;

(b) permitting natural cross pollination to occur between the corn inbred and the first high oil source;

(c) harvesting the resulting seeds produced on the male sterile plants to obtain corn primary hybrid seed;

(d) planting in pollinating proximity the corn primary hybrid seed and seed of a second high oil source to obtain corn plants, wherein either the corn primary hybrid or the second high oil source has been rendered male sterile prior to pollination;

(e) permitting natural cross pollination to occur between the corn primary hybrid and the second high oil source; and (f) harvesting the resulting seeds produced on the male sterile plants to obtain hybrid corn seed;

wherein the first and second high oil sources are selected from the group consisting of P20 having ATCC Accession No. 97872, ASKC28 having ATCC Accession No. 75105, P22 having ATCC Accession No. 97871, P58 having ATCC Accession No. 97868, UHOC3-51 having ATCC Accession No. 97969, P39 having ATCC Accession No. 97023 and P39A having ATCC Accession No. 97696, wherein the first high oil source and second high oil source are the same or different.

* * * * *